US008539838B2

United States Patent
Yoo et al.

(10) Patent No.: US 8,539,838 B2
(45) Date of Patent: Sep. 24, 2013

(54) EXTENDED FIELD OF VIEW ULTRASONIC IMAGING WITH A TWO DIMENSIONAL ARRAY PROBE

(75) Inventors: Yangmo Yoo, Mukilteo, WA (US); James Jago, Seattle, WA (US); Jing-Ming Jong, Seattle, WA (US); Robert Randall Entrekin, Kirkland, WA (US); Martin Anderson, Bothell, WA (US); Lars Jonas Olsson, Woodinville, WA (US)

(73) Assignee: Koninklijke Philips N.V., Eindhoven (NL)

( * ) Notice: Subject to any disclaimer, the term of this patent is extended or adjusted under 35 U.S.C. 154(b) by 319 days.

(21) Appl. No.: 12/995,191

(22) PCT Filed: Jun. 2, 2009

(86) PCT No.: PCT/IB2009/052321
§ 371 (c)(1),
(2), (4) Date: Nov. 30, 2010

(87) PCT Pub. No.: WO2009/147620
PCT Pub. Date: Dec. 10, 2009

(65) Prior Publication Data
US 2011/0079082 A1    Apr. 7, 2011

Related U.S. Application Data

(60) Provisional application No. 61/058,949, filed on Jun. 5, 2008.

(51) Int. Cl.
*G01N 29/00* (2006.01)
*A61B 8/00* (2006.01)

(52) U.S. Cl.
USPC .................................. 73/632; 73/618; 600/443

(58) Field of Classification Search
USPC .................. 73/632, 618, 633; 600/437, 443, 600/447, 459
See application file for complete search history.

(56) References Cited

U.S. PATENT DOCUMENTS

| | | | |
|---|---|---|---|
| 5,655,535 A | 8/1997 | Friemel et al. | |
| 5,782,766 A | 7/1998 | Weng et al. | |
| 6,102,865 A | 8/2000 | Hossack et al. | |
| 6,238,345 B1 * | 5/2001 | Wissler et al. | 600/443 |
| 6,299,579 B1 * | 10/2001 | Peterson et al. | 600/443 |
| 6,503,201 B1 * | 1/2003 | Liu et al. | 600/443 |
| 6,554,770 B1 * | 4/2003 | Sumanaweera et al. | 600/443 |
| 6,572,549 B1 * | 6/2003 | Jong et al. | 600/443 |
| 6,582,367 B1 * | 6/2003 | Robinson et al. | 600/443 |
| 6,730,031 B2 * | 5/2004 | Liu et al. | 600/443 |
| 7,756,304 B2 * | 7/2010 | Hossack et al. | 382/128 |
| 7,837,624 B1 * | 11/2010 | Hossack et al. | 600/443 |

(Continued)

*Primary Examiner* — J M Saint Surin (57) ABSTRACT

An ultrasonic diagnostic imaging system produces an extended field of view (EFOV) image. A 3D imaging probe is moved along the skin of a patient above the anatomy which is to be included in the EFOV image. As the probe is moved, images are acquired from a plurality of differently oriented image planes such as a sagittal plane and a transverse plane. As the probe is moved the image data of successive planes of one of the orientations is compared to estimate the motion of the probe. These motion estimates are used to position a succession of images acquired in one of the orientations accurately with respect to each other in an EFOV display format. The display format may be either a 2D EFOV image or a 3D EFOV image.

15 Claims, 8 Drawing Sheets

(56) References Cited

U.S. PATENT DOCUMENTS

| | | | |
|---|---|---|---|
| 8,007,439 B2 * | 8/2011 | Specht | 600/459 |
| 8,083,679 B1 * | 12/2011 | Azuma et al. | 600/443 |
| 2003/0114755 A1 | 6/2003 | Jong et al. | |
| 2004/0254466 A1 | 12/2004 | Boner et al. | |
| 2005/0033173 A1 | 2/2005 | Von Behren et al. | |
| 2006/0241434 A1 | 10/2006 | Shimazaki | |
| 2007/0255137 A1 | 11/2007 | Sui et al. | |

* cited by examiner

EXTENDED FIELD OF VIEW ULTRASONIC IMAGING WITH A TWO DIMENSIONAL ARRAY PROBE

This invention relates to medical diagnostic ultrasound systems and, in particular, to ultrasound systems which perform panoramic or extended field of view (EFOV) imaging.

Two-dimensional extended field of view (EFOV) or panoramic ultrasound imaging is a useful tool for visualizing large or long structures (e.g., femoral artery, carotid artery), which cannot be entirely viewed in conventional ultrasound imaging. In two-dimensional (2D) panoramic imaging, a large number of 2D images are acquired by manually sweeping a probe having a one-dimensional ultrasonic transducer array along the plane of the 2D image (the azimuth dimension) as described in U.S. Pat. No. 6,442,289 (Olsson et al.) The acquired overlapping images are combined to produce a panoramic image by utilizing probe motion estimates, which are typically measured by assessing registration between consecutive overlapping images. The extra-long images can be advantageously viewed on a wide aspect ratio display as shown in U.S. Pat. No. 6,516,215 (Roundhill). One limitation of conventional extended field of view imaging using a 1-D ultrasonic transducer is that motion is only tracked along one imaging plane, which is assumed to be aligned with the direction of motion. If the direction of motion is not aligned with the imaging plane of the transducer, there will be geometric distortion in the panoramic image and reduced potential for accurate measurements.

Another way to image long structures is through free-hand scanning. In free-hand scanning an ultrasound probe is manually scanned in a direction perpendicular to the plane of the image (i.e., in the elevational dimension) to acquire a series of images from different planes which are approximately parallel to each other. These images can be combined to create a three-dimensional (3D) volume known as a free-hand 3D imaging. Free-hand scanning is described in U.S. Pat. Re. 36,564 (Schwartz et al.) Free-hand 3D imaging has the ability to display anatomical structures from different orientations and planes, instead of requiring the clinician to mentally interpret the 3D orientation of the structure from 2D images. Free-hand 3D scanning can generate volumes whose size is limited only by the size of accessible acoustic windows and data storage of the ultrasound system, and so has several clinical advantages over conventional 3D ultrasound imaging in which the volume size is limited by the maximum mechanical or electronic sweep angle of the probe.

If precise measurements of distances or volumes are to be made from a free-hand 3D panoramic image, the image acquisition should be calibrated so that the sizes and orientations of structures are geometrically accurate. In calibrated 3D panoramic imaging, probe motion tracking and reconstruction are important for producing a calibrated volume. The tracking of an ultrasound probe provides motion estimates, which are directly used to compensate for the probe motion during the sweeping of the probe. Reliable 3D volume reconstruction is also critical to minimize image quality loss associated with artifacts. Furthermore, it is also important to provide real-time user feedback for assisting scanning over target structures.

Free-hand acquisition with a 1D array probe has been proposed for 3D panoramic imaging in, for instance, U.S. Pat. No. 5,899,861 (Friemel et al.) and U.S. Pat. No. 6,572,549 (Jong et al.). In this approach, probe motion is tracked by evaluating the rate of decorrelation of speckle patterns in sequentially-acquired images from different elevational planes. However, it is necessary for the speckle patterns to remain partially correlated in successive images which may not always be possible, especially during rapid sweeping of the probe. Also, motion estimates based on speckle de-correlation are not very reliable and are strongly influenced by artifacts such as those from bright specular reflectors. For more reliable motion tracking, external positioning sensors (e.g., magnetic or optical) can be attached to a 1D array probe as described in U.S. Pat. No. 6,517,491 (Thiele et al.) However these tracking devices suffer from interference and low sensitivity and can exhibit poor accuracy. The approach also requires that additional equipment to be attached to both the probe and the system, which is inconvenient.

Recently, mechanical 1D array probes have been superseded by the introduction of electronically-steered 2D array probes. A two-dimensional array transducer can electronically scan a volumetric region over three dimensions by phased steering of the beams. It is not necessary to mechanically sweep the probe over the body to acquire a 3D image, and there are no moving parts in the probe. A 2D array probe can produce 3D volumetric images in real time, and can also acquire smaller three dimensional volumes which are stitched together to produce a larger volume image with coordinated looping display of blood flow as described in U.S. Pat. No. 5,993,390 (Savord et al.) However, 2D array probes have the same limitation as mechanical 1D array probes, which is a field of view limited to the region below the probe.

Yet another approach to 3D imaging are recently proposed I-beam or E-beam probes, which contain a primary imaging array and two or three adjacent perpendicular tracking arrays as described in U.S. Pat. No. 6,102,865 (Hossack et al.) However, this approach is limited in that it can only estimate the probe motion in prearranged directions set by the orientation of the tracking arrays. Moreover, such systems are expensive since multiple array must be fabricated in a single probe and operated simultaneously. Probe position accuracy is limited by the sizes of the tracking arrays, which are usually much smaller than the imaging array.

In accordance with the principles of the present invention, multiple planar images are acquired using electronic beam steering from a 2D array probe. These planar images are used to acquire an extended field of view image or volume while simultaneously tracking probe motion in multiple directions. In a preferred embodiment, free-hand 3D panoramic images are created and displayed with a 2D array probe which can electronically steer the beam in any arbitrary image plane. A series of planar images comprised of B-mode and/or color Doppler (e.g., velocity, power and/or variance) from a primary plane are acquired during a manual sweep of a 2D array probe over target objects. Ultrasound data from that plane and, if desired, other planes also, is acquired and used to track probe motion by computing registration between consecutive images acquired along those planes. Motion estimates from each plane are combined to find the overall motion vector of the probe. The overall motion estimate is used to compensate for probe motion in reconstructing a calibrated volume from primary planar images. In accordance with a further aspect of the present invention, partial volumes are displayed during the sweep of a 2D array probe for real-time user feedback. In another embodiment, one or more planar images are displayed to show the progress of scanning. In addition, the images from a primary plane can be displayed along with a 2D panoramic image generated from one or more of the motion estimation planes. In accordance with another aspect of the present invention, an icon is displayed during the sweep of the probe to inform the clinician as to the speed and/or direction of probe motion.

Figure 1:
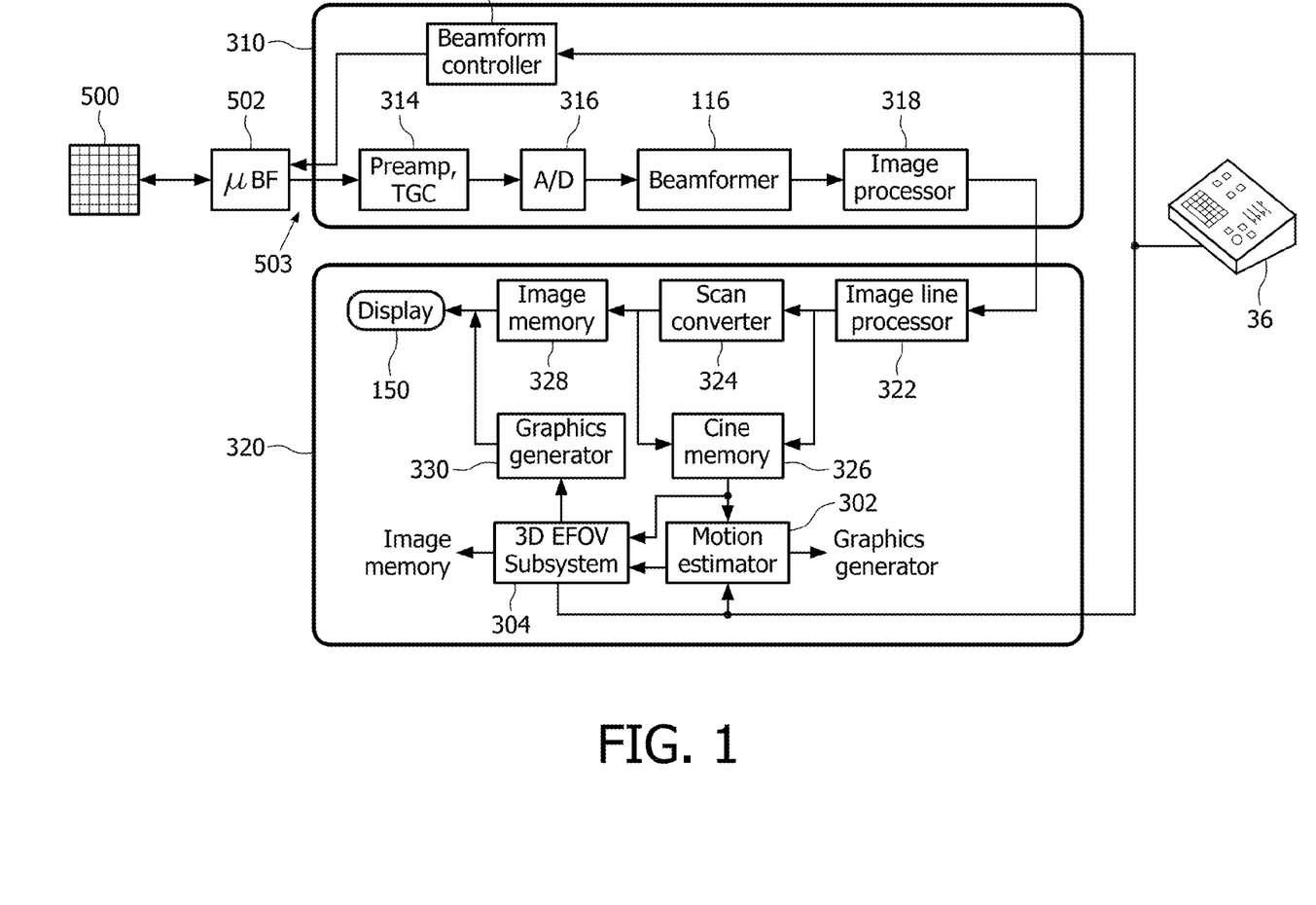
FIG. 1 illustrates in block diagram form an ultrasonic diagnostic imaging system constructed in accordance with the principles of the present invention.

Referring first to FIG. 1, an ultrasound system constructed in accordance with the principles of the present invention is shown in block diagram form. A probe is coupled to the system which includes a two-dimensional array transducer 500 and a micro-beamformer 502. The micro-beamformer contains circuitry which control the signals applied to groups of elements ("patches") of the array transducer 500 and does some processing of the echo signals received by elements of each group. Micro-beamforming in the probe advantageously reduces the number of conductors in the cable 503 between the probe and the ultrasound system and is described in U.S. Pat. No. 5,997,479 (Savord et al.) and in U.S. Pat. No. 6,436,048 (Pesque).

The probe is coupled to the scanner 310 of the ultrasound system. The scanner includes a beamform controller 312 which is responsive to a user control 36 and provides control signals to the microbeamformer 502 instructing the probe as to the timing, frequency, direction and focusing of transmit beams. The beamform controller also control the beamforming of echo signals received by the scanner by its control of analog-to-digital (A/D) converters 316 and a beamformer 116. Echo signals received by the probe are amplified by preamplifier and TGC (time gain control) circuitry 314 in the scanner, then digitized by the A/D converters 316. The digitized echo signals are then formed into fully steered and focused beams by a beamformer 116. The echo signals are then processed by an image processor 318 which performs digital filtering, B mode detection, and Doppler processing, and can also perform other signal processing such as harmonic separation, speckle reduction through frequency compounding, and other desired image processing.

The echo signals produced by the scanner 310 are coupled to the display subsystem 320, which processes the echo signals for display in the desired image format. The echo signals are processed by an image line processor 322, which is capable of sampling the echo signals, splicing segments of beams into complete line signals, and averaging line signals for signal-to-noise improvement or flow persistence. The image lines are scan converted into the desired image format by a scan converter 324 which performs R-theta conversion as is known in the art. The image is then stored in an image memory 328 from which it can be displayed on a display 150. The image in memory is also overlaid with graphics to be displayed with the image, which are generated by a graphics generator 330 which is responsive to the user control 36. Individual images or image sequences can be stored in a cine memory 326 during capture of image loops or sequences.

For real-time volumetric imaging the display subsystem 320 also includes a 3D image rendering processor in a 3D EFOV subsystem 304 (described more fully in FIGS. 8 and 9) which receives image lines from the image line processor 322 for the rendering of a real-time three dimensional image which is coupled to the image memory 328 for display on the display 150.

In accordance with the principles of the present invention the 3D EFOV subsystem produces images for extended field of view imaging. The EFOV images can be two dimensional planar images as described in the aforementioned Olsson et al. and Roundhill patents, or can be 3D images. The EFOV images are assembled by estimating the probe motion in a motion estimator 302 using the image data provided by cine memory 326. The motion estimator can track the movement of the probe along the body of a patient by registering the data of successively acquired images, for example by using a technique called MSAD block matching as described in U.S. Pat. No. 6,299,579 (Peterson et al.) Other motion estimation techniques such as non-rigid body registration can be used if desired. The block matching technique computes the displacement between successively acquired images which are at least partially overlapping. When the displacement is computed of images in different planar orientations, a displacement vector of both magnitude and direction can be computed in three dimensions by the motion estimator 302. The displacement vector provides position information to the EFOV subsystem 304 for relatively positioning images acquired from different planes as the probe is moving. When the successive images are properly located with respect to each other by the EFOV subsystem, a geometrically accurate two or three dimensional EFOV image is produced.

Figure 2:
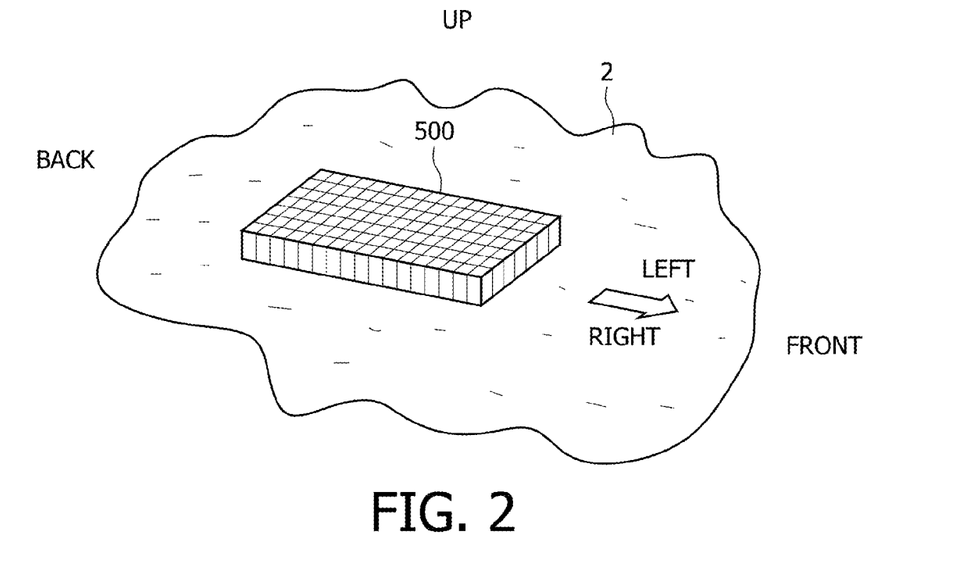
FIG. 2 illustrates a 2D array transducer being moved over the skin of a subject.

The EFOV imaging technique of the present invention may be more fully understood by referring first to FIG. 2, which is a perspective view depicting the motion of a 2D array probe as it acquires an EFOV image. Shown is the 2D array transducer 500 with the surrounding probe case and transducer stack removed for clarity of illustration. In this drawing the 2D array transducer 500 is moving along the skin surface 2 of a patient and is acquiring image data as it moves. The 2D array transducer is moving in the direction of the large arrow, which is in the "FRONT" direction and away from the "BACK" direction behind the probe. To either side of the direction of motion are the "LEFT" and "RIGHT" directions.

Figure 3:
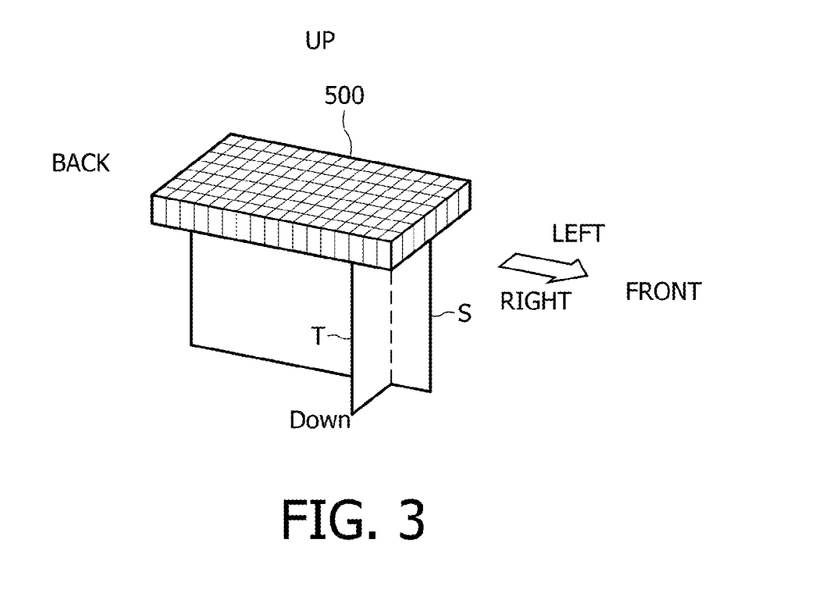
FIG. 3 illustrates the acquisition of ultrasound information in two planes as a 2D array transducer is being moved.

With these directional references in mind, reference is now made to FIG. 3, which shows two planes "S" (sagittal) and "T" (transverse) in which images are acquired as the probe moves in the direction indicated by the arrow. The two planes are depicted in this example as being rectangular in shape, although in a given embodiment they may have other formats such as sector or trapezoidal shapes. The two planes S and T are seen extending in the "DOWN" direction from the 2D array transducer 500. While the 2D array transducer 500 is capable of scanning many more image planes and indeed the full volume below the array transducer, in this embodiment it is only necessary to scan the two S and T planes. The need to scan only two planes means that images can be rapidly acquired in quick succession by alternating or interleaving the scanning of the two planes. A high acquisition frame rate means that relatively little motion will have occurred between images and there will be significant overlap in the image data content of successive images, improving the ability to find the similarity in the image data and calculate the motion vector, and also improving spatial sampling for later reconstruction of a calibrated volume. The displacement between successive images can be accurately estimated and a geometrically precise EFOV image assembled by correct location of the images with respect to each other.

In the example of FIG. 3, two types of EFOV images can be formed. One is formed of the succession of S plane images acquired as the 2D array transducer moves in the direction of the arrow. Movement in the BACK to FRONT direction will be reflected in the image content of successively acquired S plane images. Movement UP and DOWN will also be reflected in the image content of the S plane. The displacement between successive T plane images will reveal movement in the LEFT or RIGHT directions, and also UP and DOWN. Thus, these displacement estimates are used to produce a vector of the relative displacement from one S plane image to the next. The succession of S plane images are then overlaid in alignment and stitched together to produce a two dimensional EFOV image with its longest dimension being in the direction of the arrow. It is important to note that, unlike conventional EFOV imaging using a 1-D transducer, according to the principles of the present invention it is not necessary for the probe motion to be aligned exactly with the S plane. Even if the motion deviates from this plane, this deviation will be tracked by the T plane so that a well calibrated panoramic image can be generated.

The other EFOV image that can be acquired in the example of FIG. 3 is a 3D EFOV image compiled from successively acquired T plane images. The displacement vector between successively acquired T plane images is calculated from the S and T plane image information as previously described, then used to properly locate successive T plane images with respect to each other. As T plane images continue to be acquired in the direction of the arrow, the thickness of the three dimensional image in the direction of the arrow grows as more T planes of successive displacement are in FRONT of the previously acquired and positioned images. The 3D EFOV image thus has its longest dimension normal to the T plane.

It is possible to produce both images at the same time, since planar images are constantly being acquired for both the 2D EFOV and the 3D EFOV images. For instance, an extended volumetric image can be acquired of the tissue intercepted by successive T plane images, and an extended cut plane down the center of this volume can be produced by an EFOV of successive S planes. The S and T planes do not need to be associated with particular dimensions of the physical transducer array 500, but can be acquired with the S plane oriented along either dimension, with the T plane perpendicular to this. The S plane does not need to be centered under the 2D array as shown in FIG. 3, but can be acquired to either side of center or at an angular tilt to form an EFOV image of a differently oriented cut plane of the 3D volume of the 3D EFOV image. Depending on the choice of apertures for the S and T planes, the T plane may not necessarily be perpendicular to the S plane.

The example of FIG. 3 adds a third acquisition plane, a "C" (cross-sectional) plane as planes parallel to the major plane of the two dimensional array are known. The displacement between successive images of the C plane is calculated as described above, and will indicate motion of the 2D array transducer in both the BACK to FRONT and the LEFT and RIGHT directions. With successive T plane images providing displacement information in the UP and DOWN directions, it is seen that a three dimensional displacement vector can be computed without the need for any information from the S plane. This means that, for a 2D EFOV image compiled from images from the S plane, the S plane acquisition can be optimized for imaging and the T and C plane acquisition can be optimized for displacement measurement. Alternatively, if successive T plane images are to be assembled in a 3D EFOV image, the C and S plane acquisitions can be optimized for displacement measurement while the T plane acquisitions are optimized for imaging. The sizes of the displacement measurement images can be made smaller or their line spacing increased, for example, while the image plane is kept large and with high line density for a high resolution image.

Figure 4:
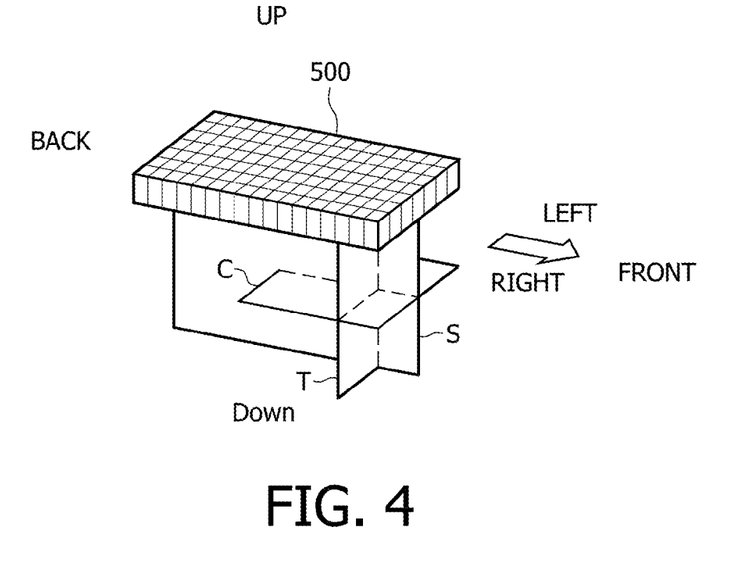
FIG. 4 illustrates the acquisition of ultrasound information in three planes as a 2D array transducer is being moved.

It is also possible in the example of FIG. 4 to assemble a 2D EFOV image from successive C plane images, if desired. When a C plane is acquired, the volume data between the C plane and the probe is obtained without any additional acoustic transmission. The successive sequences of volume data can be aligned by 3D registration to find the six degree of freedom of the probe (three translation and three rotation) in the entire acquisition process, which allows accurate reconstruction of either a 3D or a 2D EFOV image.

It will be appreciated that motion which is normal to a plane will cause the image content of the image plane to rapidly decorrelate from one plane to another, making displacement estimation in that direction problematic. However, the use of multiple, differently oriented planes enables such elevational displacement to occur in the plane of another image, where image to image correlation will remain high and displacement can still be accurately estimated.

Figure 5:
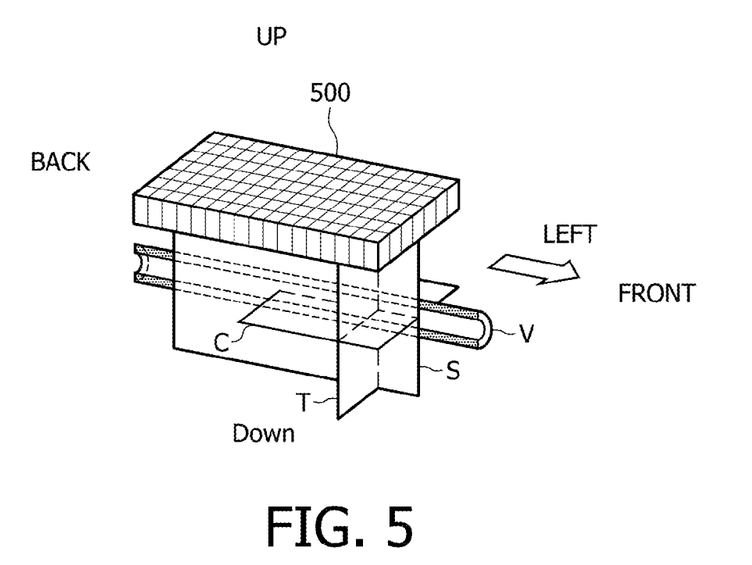
FIG. 5 illustrates the image acquisition technique of FIG. 4 to image a blood vessel of extended length.

FIG. 5 depicts the EFOV scanning of a blood vessel V in the body by use of the T, S, and C planes. In this example an EFOV image is produced over a considerable length of the blood vessel V, enabling much or all of the characteristics of the vessel to be diagnosed in a single image. As the 2D array transducer probe is moved, the S plane is kept in alignment with the center of the blood vessel V so that a cut plane image down the vertical center of the vessel can be produced. The depth of the C plane is set so that this plane will continue to intersect the horizontal center of the blood vessel if the vessel remains at a constant depth in the body. The T plane continues to intercept the blood vessel and its surrounding tissue as the probe moves. This arrangement can be used, for instance, to simultaneously produce multiple EFOV images, a 3D EFOV image of the blood vessel V from successive T plane images, and orthogonally oriented 2D cut planes from successive T and C plane images.

Figure 6A:
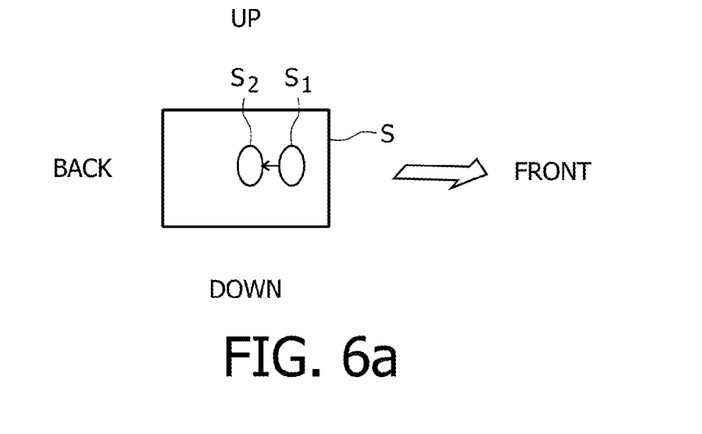
FIGS. 6a-6c illustrate the change in position of image structures in different planes as the 2D array transducer acquiring the images is moving.
Figure 6B:
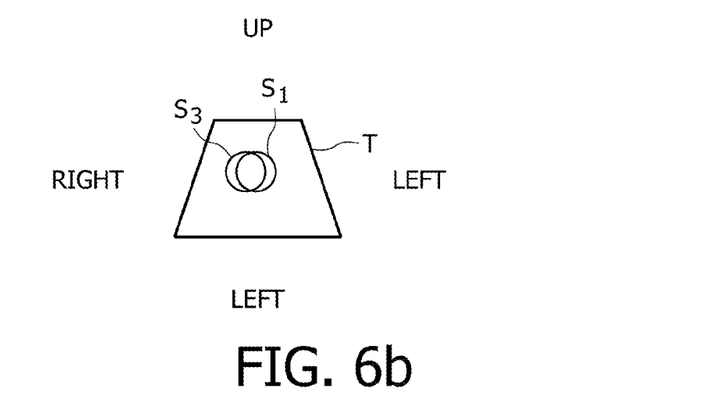
Figure 6C:
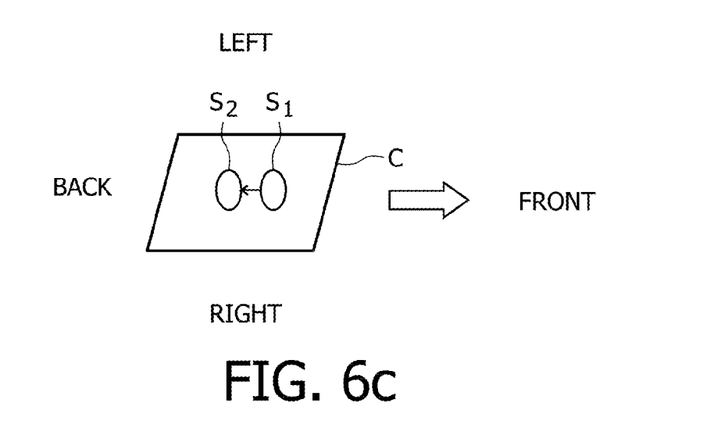

FIGS. 6a-6c depict the different in-plane displacements that can be readily determined from successions of the differently oriented planes. As FIG. 6a shows, a structure $s_1$ which appears to the FRONT in one S image will appear to have moved to the BACK in the next successive S plane image when the probe is moving in the direction of the arrow, as indicated by the small arrow between the successive positions $s_1$ and $s_2$ of the structure. Displacements of the structure UP and DOWN will also readily be discernible from the relative positions of the structure in the successive images. FIG. 6B shows that the position of the $s_1$ structure in one T plane image will change to the $s_2$ position in a successive T plane image when the probe moves to the LEFT. UP and DOWN displacement can also be readily discerned from successive T plane images. Successive C plane images will readily reveal FRONT to BACK movement of the probe, as well as LEFT and RIGHT movement, as shown in FIG. 6c.

Figure 7:
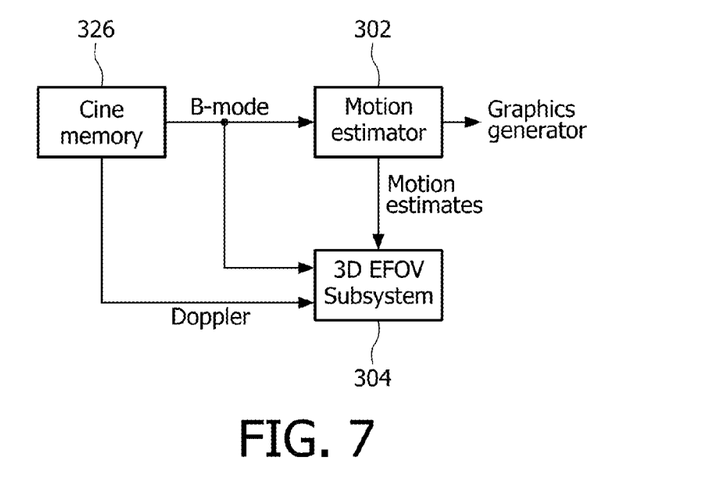
FIG. 7 is a more detailed block diagram of the motion estimation components of the ultrasound system of FIG. 1.

FIG. 7 is a block diagram showing connections between the motion estimator 302 and the 3D EFOV subsystem 304 of FIG. 1. In this embodiment the cine memory 326 stores received planar images prior to their use for EFOV images. B mode images are used for motion estimation in this example because B mode images do not exhibit the pulsation or flash artifacts of some Doppler signals. The motion estimator analyzes successive B mode images and estimates displacement vectors from image to image. These motion estimates are forwarded to the 3D EFOV subsystem where they are used to relatively align the acquired images. The images which are aligned may be Doppler images, B mode images, or both, as forwarded to the 3D EFOV subsystem from the cine memory. The motion estimator also produces motion information for the graphics generator 330 which uses the information for the display of one or more motion indication icons on the image display as described below.

Figure 8:
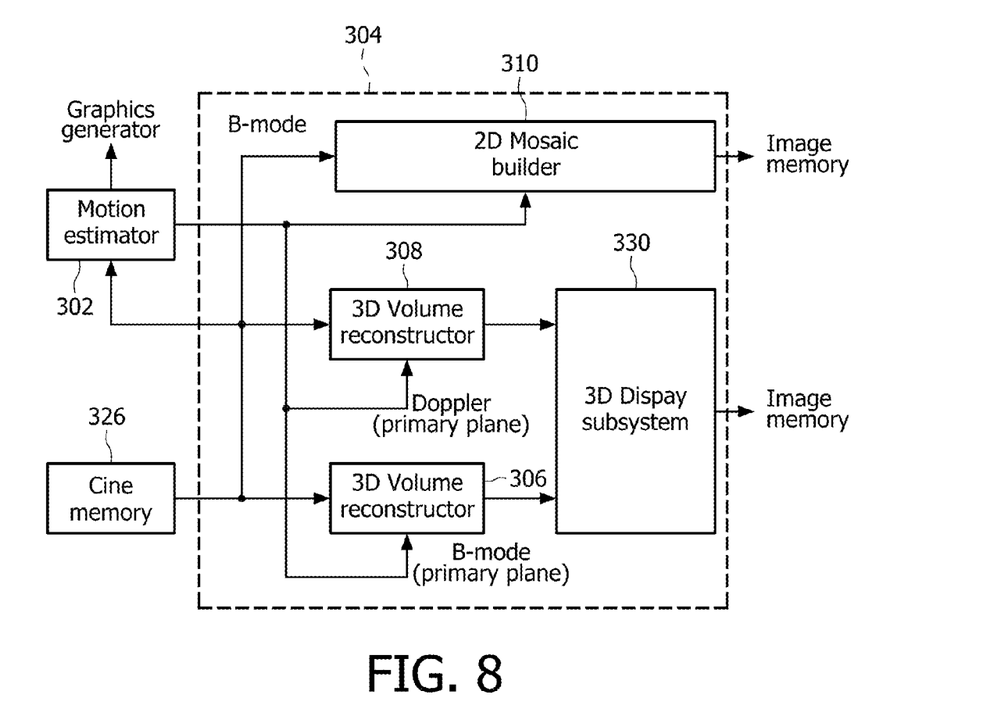
FIG. 8 is a more detailed block diagram of the EFOV subsystem of FIG. 7.

FIG. 8 is a block diagram illustrating further details of a 3D EFOV subsystem 304 constructed in accordance with the principles of the present invention. Motion estimates from the motion estimator 302 are coupled to a 2D mosaic builder 310, a 3D Doppler volume reconstructor 308, and a 3D B mode volume reconstructor 306. B mode images stored in cine memory 326 are supplied to the 2D mosaic builder 310, the motion estimator 302, and the 3D B mode volume reconstructor 306. Doppler images are supplied to the 3D Doppler volume reconstructor 308. The 3D volume reconstructors function in the same manner as the 3D image renderer described in U.S. Pat. No. 5,572,291 (Schwartz) in which a 3D image is rendered from a plurality of 2D images oriented with respect to each other as guided by the motion estimates of the motion estimator. One or both 3D renderings, depending upon the image information supplied, are coupled to a 3D display subsystem 330 where tissue and flow images of the B mode and Doppler renderings can be merged together for a 3D image of both tissue and flow as described in the '291 patent. Various 3D visualization enhancements can also be applied in the 3D display subsystem, such as multiplanar reconstruction and surface rendering. The 3D image is supplied to the image memory 328 for display. The 2D mosaic builder 210 combines partially overlapping 2D image frames to form a 2D EFOV image as described in the aforementioned Olsson et al. patent. The 2D EFOV image is supplied to the image memory 328 also from which it may be displayed independently or together with the 3D EFOV image of the 3D display subsystem 330. For instance, the 3D display subsystem 330 can provide a 3D EFOV image of a volume in the body while the 2D mosaic builder provides a 2D EFOV image of a planar slice through the 3D volume.

Figure 9:
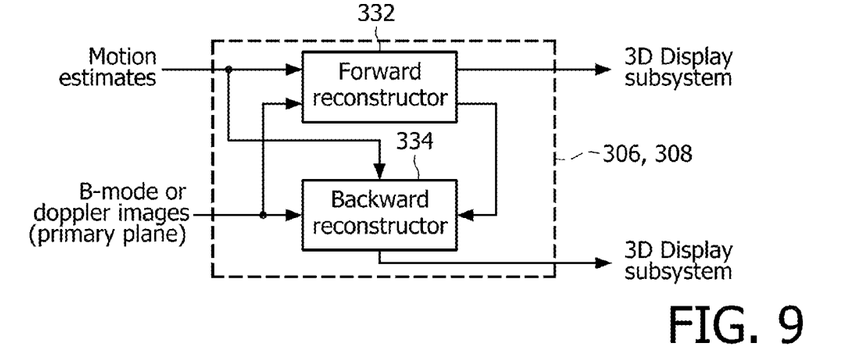
FIG. 9 is a more detailed block diagram of the 3D volume reconstructor of FIG. 8.

FIG. 9 is a block diagram illustrating further details of a 3D volume reconstructor of an embodiment of the present invention. The illustrated 3D volume reconstructor 306,308 can simultaneously form 3D images with both forward and backward data mapping by means of a forward reconstructor 332 and a backward reconstructor 334. A 3D volume is reconstructed with forward mapping where input data are directly mapped into output voxels depending on transformation matrices which are provided by the motion estimation. While this approach can provide fast response with potentially the same resolution as an input 2D image, since new image data is added to the rendered volume as soon as it is received, the resulting 3D image may have holes in the reconstructed volume. On the other hand, the backward mapping method of the backward reconstructor utilizes inverse transformation matrices so that more detailed output voxels are generated from input data by means of interpolation. With the backward mapping 3D reconstruction, fewer holes appear in the reconstructed volume but the response is slower because reconstruction must await all of the input data from the scan before inter-plane image data can be interpolated. A suitable interpolation method which can be used is expressed by $$Q_0 = \frac{d_1}{d_1 + d_2} Q_2 + \frac{d_2}{d_1 + d_2} Q_1$$

where $Q_0$ is an interpolated pixel value between two acquired pixels $Q_1$ and $Q_2$ which is separated from the acquired pixels by distances $d_1$ and $d_2$, respectively. Other higher order interpolation techniques such as polynomial and spline interpolation may alternatively be used. The illustrated embodiment offers both forward and backward reconstruction so that the user has the choice of a faster or a more detailed reconstruction for display.

Figure 10A:
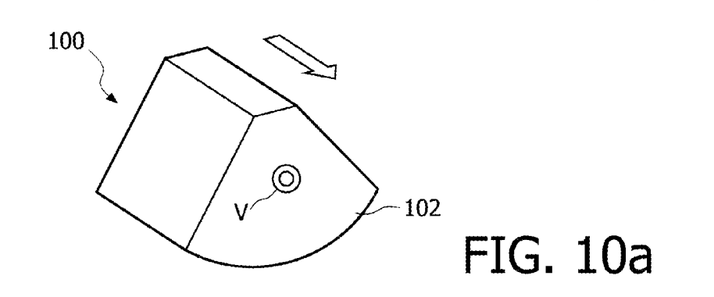
FIGS. 10a-10d illustrate the development of a 3D EFOV image using a 2D array probe in accordance with the present invention.
Figure 10B:
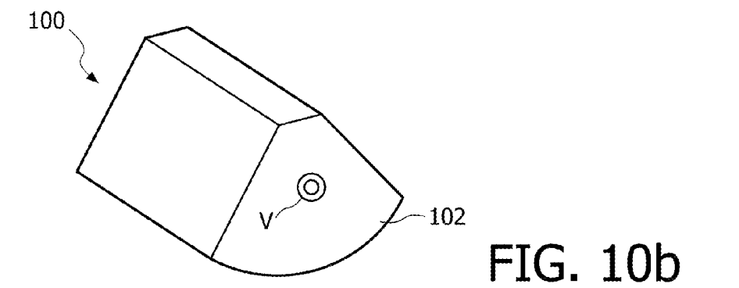
Figure 10C:
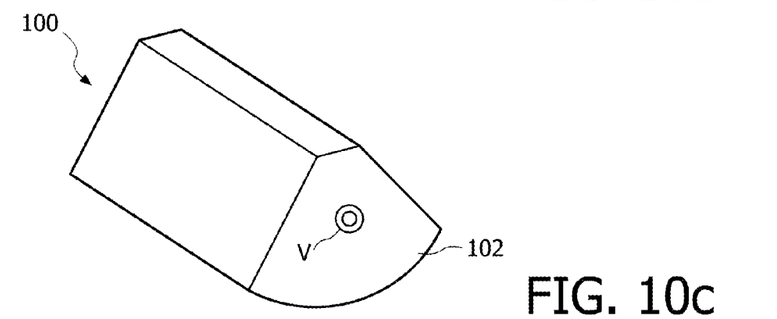
Figure 10D:
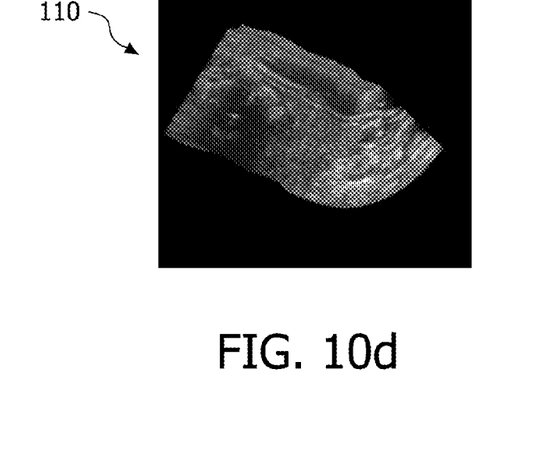

FIGS. 10a-10d illustrate how a 3D EFOV image appears on the ultrasound system display as a patient is being scanned. As the probe is moved in the direction indicated by the arrow in FIG. 10a, image planes which bisect a blood vessel V are successively added to the front surface of the volume 100 being scanned and displayed. As the probe continues its movement along the skin of the patient, more and more planes are scanned and added to the front of the volume and the volume grows in this dimension as shown in the longer EFOV volume 100 of FIG. 10b. As the probe moves even further, more planes to the front are added to the volume, which grows even more as depicted in FIG. 10c. As previously explained, each new plane is located with respect to the previous planes of the volume by estimating the motion and hence the displacement from the last acquired plane to the current one. This displacement information may be computed from the image data of one or more orthogonal scan planes such as image plane C or S as illustrated in FIGS. 3, 4, and 5. Each newly acquired plane is thus added in consideration of its correct geometrical relationship to the previously acquired planes and the volume. The resulting volume is thus geometrically accurate and capable of supporting quantified measurements of the structure shown in the volume. FIG. 10d is an illustration of an actual 3D EFOV image acquired and produced in accordance with the present invention. (The black-white grayscale range of pixels of the image has been reversed from its normal white-on-black in FIG. 10d for clarity of illustration.)

Figure 11:
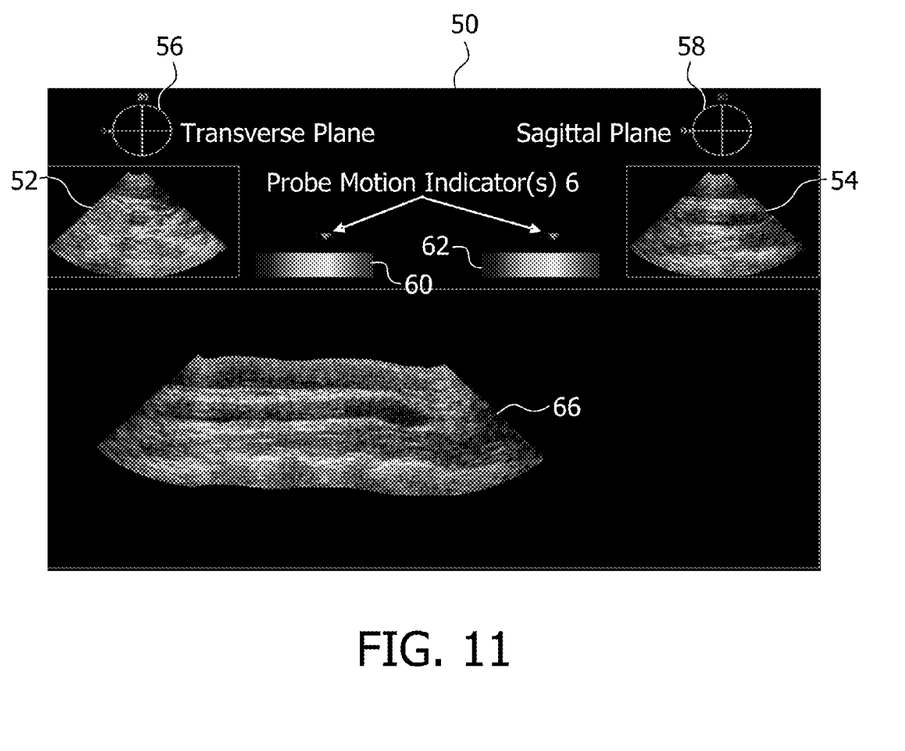
FIG. 11 illustrates a display produced by an ultrasound system of the present invention with probe motion indicators which indicate the scanning speed.

FIG. 11 illustrates an EFOV display 50 of an ultrasound system constructed in accordance with the principles of the present invention which provides guidance to the clinician who is moving the ultrasound probe to acquire an EFOV image. In this example a 2D EFOV image 66 is compiled from a succession of component images acquired in the sagittal plane S of FIG. 3. As the probe moves, component images are continually acquired in both the sagittal S and transverse T planes. Images in both planes are used by the motion estimator 302 to track the movement of the probe. Some or all of the transverse and sagittal component images are shown at the top of the display, with 52 being a recently acquired transverse plane image and 54 being a recently acquired sagittal plane image. Graphic icons 56 and 58, produced by the graphics generator 330, are displayed above the component images 52 and 54 and contain a bar which is highlighted in color to indicate the respective plane orientation. In this example the orientation is indicated as if the plane were being viewed edge-on from above the transducer 500.

In accordance with the principles of the present invention, two probe motion indicators 6 are shown in the center of the display 50. Each probe motion indicator has a colored bar 60, 62 which delineates a range, and a small triangle (indicated by arrows) which indicates a point in the range. In this example each probe motion indicator provides an indication to the clinician of the speed at which the probe is moving, the two illustrated indicators being for transverse and sagittal motion, respectively. The position of the graphic triangle above each bar is computed from the frame to frame displacement estimated by the motion estimator 302 and the known times at which the frames were acquired. Knowledge of these time and distance values enables a direct estimation of velocity in a given direction. In this example, since the clinician is performing EFOV scanning by moving the probe in the FRONT sagittal direction as shown in FIG. 3, the transverse motion indicator tells the clinician whether the motion of his probe is in a straight line along the body or is drifting to the LEFT or to the RIGHT. When the small triangle remains centered over the color bar 60, the probe is moving in a straight line to the FRONT in this example. This means that each successive sagittal component image used to form the EFOV image 66 is in substantially the same image plane. But if the probe begins to move to the LEFT or the RIGHT, successive component images will not be co-planar and the small triangle will correspondingly move to the left or the right of the color bar center to indicate this motional deviation. The faster the probe moves to the LEFT or the RIGHT, the greater the displayed deviation of the small triangle from the center of the color bar. When the probe resumes movement in a straight line to the FRONT, the small triangle will return to and remain centered again.

The sagittal probe motion indicator including color bar 62 will indicate velocity in the FRONT direction in this example. Before the scan begins and the probe is at rest on the patient, the small triangle is above the far left side of color bar, the zero velocity point. As the clinician begins to move the probe and its speed increases, the small triangle begins to move to the right to indicate the speed of the probe in the sagittal FRONT direction. For a uniform EFOV image it is desirable to move the probe at a constant speed so that the component images are acquired at substantially evenly spaced temporal and spatial intervals. Using parameters available in a given embodiment such as the desired length of the image, the amount of cine memory available, the amount of component image overlap, and the like, the clinician can set up his system so that the small triangle will be centered over the color bar when the probe is being moved at the desired speed. Thus, to scan a straight expanse of anatomy at the desired speed, the clinician only needs to see that the two small triangles both stay in the center over their respective color bars as the probe is being moved. By maintaining this positioning of the small triangles, the clinician will obtain the high quality EFOV image she desires. Since some users may intently watch the displayed image during acquisition, it is also possible to provide an audible alarm, such as bell sound, when the probe is moving too fast or too slow.

It will be appreciated that one or both of the probe motion indicators can be denominated in units other than velocity. For example the clinician could decide to acquire an EFOV image over a distance on the body of 50 cm. The sagittal probe motion indicator bar 62 could then be set to indicate progress toward this distance, starting from zero at the left side of the color bar 62 and continuing to a covered distance of 50 cm at the right. As the clinician commences the scan the small triangle will continue to move with the displacement of the probe from its starting point. When the small triangle has moved all the way to the right end of the color bar, the clinician will know that the 50 cm of scanning has been completed. Another unit in which the probe motion indicators can be denominated is time, for example.

Figure 12:
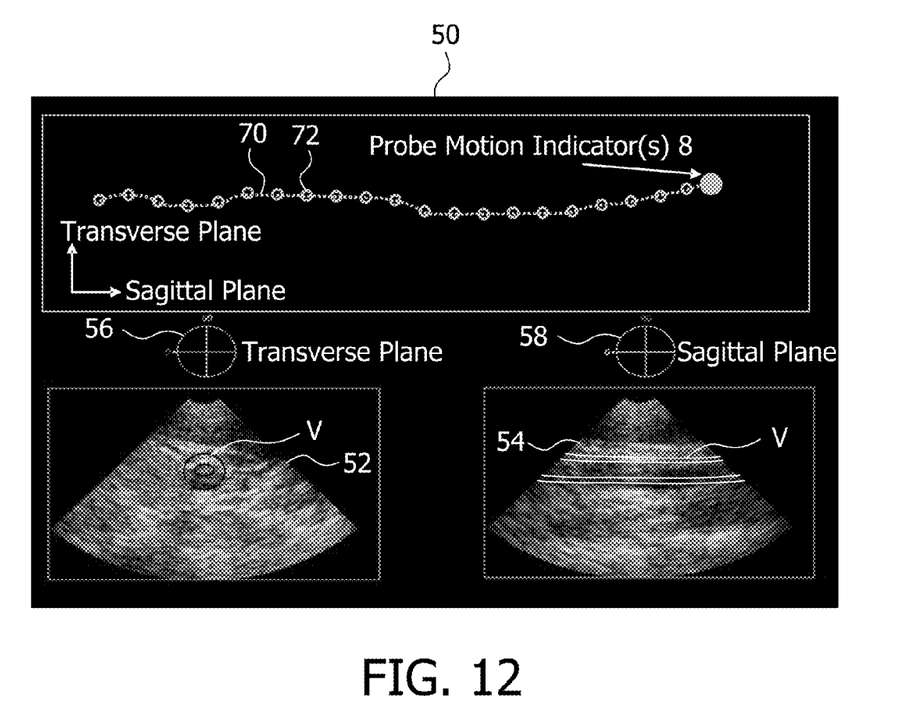
FIG. 12 illustrates another display produced by an ultrasound system of the present invention with a probe position indicator which indicates scanning progress.

FIG. 12 illustrates a second EFOV display 50 of an ultrasound system constructed in accordance with the principles of the present invention which provides guidance to the clinician who is moving the ultrasound probe to acquire an EFOV image. In this example the display does not show the EFOV image as it is developing, but only shows the component images 52 and 54 as they are acquired. It is the component images which are used by the motion estimator to track the movement of the probe. As in the previous example the plane orientation icons 56, 58 are shown above the respective component images 52, 54.

In the display area above the component images is displayed a graphic trace of the path traversed by the probe as an EFOV scan is performed. In this example the trace 70 is formed by a series of small dots. Orientation arrows below the trace 70 indicate the transverse (LEFT-RIGHT) and sagittal (BACK-FRONT) directions. The trace 70 is produced from the displacement estimates produced by the motion estimator 302. A series of circles 72 are put down along the trace 70 which mark 1 cm increments along the path delineated by the trace. Alternatively the circles 70 could be put down after a given number of component frames have been acquired or after another increment of time has transpired during the scan, giving the clinician a sense of the uniformity of the probe motion. At the end of the trace 70 a large dot 8 indicates the current probe position during the motion of the probe. The path of the trace 70 can be related to a specific point of the array such as by using the axis of intersection of the S and T planes and its point of origin on the 2D array as the probe location reference point.

In this example a 3D EFOV image is being compiled from the succession of transverse planes 52. In this illustrated example the volume of tissue being scanned includes a blood vessel V shown in lateral cross-section in the transverse component image 52 and in longitudinal cross-section in the sagittal component image 54. The clinician can guide her movement of the probe to keep the lateral cross-section of the blood vessel V centered in the middle of each successive transverse component image 52 as shown in the drawing, and with the succession of sagittal component images 54 continuing to show the major longitudinal cut plane of the blood vessel V. The clinician is thereby guided in the acquisition of a 3D EFOV image that fully encompasses the blood vessel V. After the guided image acquisition is complete, the clinician can switch to a view of the 3D EFOV image such as that of FIG. 10*d*.

While the preferred embodiment utilizes a 2D array transducer probe which electronically steers beams over the desired image planes as the probe is moved, it will be appreciated that the EFOV scan and image acquisition can also be performed with a mechanical 3D scanning probe that oscillates a 1D array back and forth in the probe as the probe is moved. For example the 3D mechanical probe shown in US patent publication 2004/0254466 can be used for EFOV scanning in accordance with the present invention. Each time the moving 1D array attains a given position in its oscillatory sweep, an image can be acquired in the image plane orientation of that array position. One or a few nearby elements of the array can be continually operated to continually scan an orthogonal plane as the array oscillates. As the probe is moved along the skin of the patient these two acquisitions will continually scan two different planes as the probe is moved in an EFOV scan.

What is claimed is:

1. An ultrasonic diagnostic imaging system which produces an extended field of view (EFOV) image comprising:
an ultrasound probe including a two-dimensional array transducer which may be moved along the surface of a subject;
a beamformer coupled to the array transducer which controls the probe to repeatedly scan a plurality of intersecting images in image planes of two different plane orientations with respect to the array as the probe is moved along the surface, a first plane orientation being an S plane which is substantially aligned with the direction of transducer motion and a second plane orientation being a T plane which is substantially transverse to the direction of transducer motion;
an image processor responsive to signals received from the array transducer to form sequences of images of the two different plane orientations as the probe is moved;
a motion estimator, responsive to at least one of the sequences of images which produces estimates of probe motion;
an EFOV subsystem responsive to the probe motion estimates which operates to produce an EFOV image from at least one of the sequences of images; and
a display responsive to the EFOV subsystem for displaying the EFOV image.

2. The ultrasonic diagnostic imaging system of claim 1, wherein the EFOV subsystem operates to produce a two dimensional (2D) EFOV image from a sequence of S planes.

3. The ultrasonic diagnostic imaging system of claim 1, wherein the EFOV subsystem operates to produce a three dimensional (3D) EFOV image from a sequence of T planes.

4. The ultrasonic diagnostic imaging system of claim 1, wherein the array transducer further comprises a 2D array transducer which performs electronic beam steering.

5. The ultrasonic diagnostic imaging system of claim 1, wherein the motion estimator produces estimates of probe motion by analysis of the image data of successively acquired images of a given set of plane orientations.

6. The ultrasonic diagnostic imaging system of claim 1, wherein the different plane orientations are a sagittal plane orientation and a transverse plane orientation.

7. The ultrasonic diagnostic imaging system of claim 6, further comprising a C plane orientation.

8. A method of operating the ultrasonic diagnostic imaging system of claim 1 to produce an EFOV image comprising:
moving the ultrasound probe along the surface of a subject;
repeatedly acquiring images of different and T plane orientations as the probe is moved, the image plane of each plane orientation extending from the two dimensional array transducer;
estimating the probe displacement from the images acquired in one or more of the plane orientations as the probe is moved;
using the estimates of probe displacement to produce an EFOV image from the images acquired from one of the plane orientations; and
displaying the EFOV image on the display.

9. The method of claim 8, wherein estimating further comprises comparing the image data of successively acquired images of the one plane orientation.

10. The method of claim 8, wherein using further comprises producing a two dimensional EFOV image from a succession of images acquired from a sagittal plane orientation as the probe is moved.

11. The method of claim 8, wherein using further comprises producing a three dimensional EFOV image from a succession of images acquired from a transverse plane orientation as the probe is moved.

12. The method of claim 8, wherein estimating the probe displacement further comprises estimating probe displacement from B mode images.

13. The method of claim 12, wherein using the estimates of probe displacement to produce an EFOV image further comprises producing one or both of a B mode EFOV image and a Doppler EFOV image.

14. The method of claim 8, wherein using further comprises producing an EFOV image from a succession of images acquired from a C plane orientation as the probe is moved.

15. The method of claim 8, wherein using further comprises producing a three dimensional EFOV image from a succession of images acquired from a C plane orientation and volume data between the C plane and the probe as the probe is moved.

* * * * *